(12) United States Patent
Soudant et al.

(10) Patent No.: US 7,482,032 B2
(45) Date of Patent: *Jan. 27, 2009

(54) CAROTENOID PREPARATION

(75) Inventors: Etienne Soudant, Froseca (FR); Lea Bezalel, Beer Sheva (IL); Hedva Schickler, Mazkeret Batva (IL); Judith Paltiel, Rehovot (IL); Ami Ben-Amotz, Savion (IL); Aviv Shaish, Shikmim (IL); Inon Perry, Tel Aviv (IL)

(73) Assignee: I.B.R. Israeli Biotechnology Research, Ltd., Tel Aviv (IL)

(*) Notice: Subject to any disclaimer, the term of this patent is extended or adjusted under 35 U.S.C. 154(b) by 0 days.

This patent is subject to a terminal disclaimer.

(21) Appl. No.: 10/097,730

(22) Filed: Mar. 14, 2002

(65) Prior Publication Data

US 2002/0131940 A1  Sep. 19, 2002

Related U.S. Application Data

(63) Continuation of application No. 09/786,394, filed as application No. PCT/IL99/00478 on Sep. 5, 1999, now Pat. No. 6,383,474.

(30) Foreign Application Priority Data

Sep. 4, 1998  (IL) .................................... 126076

(51) Int. Cl.
*A23L 3/00* (2006.01)
*A23L 1/30* (2006.01)

(52) U.S. Cl. .................... 426/321; 426/72; 426/73; 426/542

(58) Field of Classification Search ............... 426/72, 426/73, 321, 541, 542; 424/59, 401
See application file for complete search history.

(56) References Cited

U.S. PATENT DOCUMENTS

| 4,199,895 | A |   | 4/1980  | Avron et al. |
|---|---|---|---|---|
| 5,310,554 | A |   | 5/1994  | Haigh |
| 5,545,816 | A |   | 8/1996  | Ausich et al. |
| 5,834,044 | A | * | 11/1998 | Schmitz et al. .............. 426/73 |
| 6,132,790 | A | * | 10/2000 | Schlipalius ................ 426/540 |
| 6,383,474 | B1 | * | 5/2002 | Soudant et al. .............. 424/59 |

FOREIGN PATENT DOCUMENTS

| DE | 246 565 A1 | 6/1987 |
|---|---|---|
| EP | 0 769 551 A1 | 4/1997 |
| FR | 2 620 131 | 3/1989 |
| FR | 2 678 946 | 1/1993 |
| FR | 2 759 904 | 8/1998 |
| JP | 9040520 A2 | 2/1997 |
| WO | 93/04598 | 3/1993 |
| WO | 96/39869 | 12/1996 |

OTHER PUBLICATIONS

Delia B. Rogriguez-Amaya, Ph.D., A Guide to Carotenoid Analysis in Foods, 2001, ISBN 1-57881-072-8.*
Ben-Amotz, Ami et al. "Stereoisomers of β-Carotene and Phytoene in the Alga *Dunaliella bardawil.*" *Plant Physiol.* 86, pp. 1286-1291, 1988.
Kümmel, H.W. et al. "The Inhibition of Carotenoid Biosynthesis in Green Algae by Sandoz H 6706: Accumulation of Phytoene and Phytofluene in *Chlorella fusca*." *Z. Naturforsch.* 30, pp. 333-336, 1975.
Shaish, Aviv et al. "Effect of Inhibitors on the Formation of Stereoisomers in the Biosynthesis of β-Carotene in *Dunaliella bardawil.*" *Plant Cell Physiol.* 31(5), pp. 689-696, 1990.
Salles, Bernard et al. "A Chemiluminescent Microplate Assay to Detect DNA Damage Induced by Genotoxic Treatments." *Analytical Biochemistry.* 232, pp. 37-42, 1995.
Mathews-Roth, Micheline M. *Carotenoids: Chemistry and Biology.* Krinsky, N.I. et al., Eds. Plenum Press, New York. pp. 1-382, 1990.
Foppen, Fredrik H. "On some pigments of *Epicoccum nigrum* Link: their isolation and structure elucidation and a biosynthetic pathway of rhodoxanthin." *Ann. Ist. Super. Sanità.* 5, pp. 439-513, 1969.
Tonucci, L.H., et al. "Carotenoid Content of Thermally Processed Tomato-Based Food Products", *J. Agric. Food Chem.* vol. 43, pp. 579-586, (1995), XP-002124250.
Ben-Amotz, A., et al., "Massive Accumulation of Phytoene Induced by Norflurazon in *Dunaliella bardawil* (Chlorophyceae) Prevents Recovery From Photoinhibition", *J. Phycol.*, vol. 23, pp. 176-181, (1987), XP-000901498.
Ben-Amotz, A., et al., "The Biotechnology of Cultivating *Dunaliella* for Production of β-Carotene Rich Algae", *Bioresource Technology*, vol. 38, pp. 233-235, (1990) XP-000901780.
Vaisberg, A. and Schiff, J.A., "Event Surrounding the Early Development of Euglena Chloroplasts", *Plant Physiol.*, vol. 57, pp. 260-269, (1976).
Patent Abstracts of Japan, JP 56099405, (10.08.81).
Choo, Y.M., "Production of Palm Oil Carotenoid Concentrate and Its Potential Application in Nutrition", Chemical Abstracts, XP-002124251., 1992.

* cited by examiner

*Primary Examiner*—Leslie Wong
(74) *Attorney, Agent, or Firm*—Fennemore Craig, P.C.

(57) ABSTRACT

A preparation comprising the carotenoids phytoene and phytofluene in an amount which, in combination, is effective in preventing various kinds of damage resulting from oxidation and exposure to UV light is provided. The preparation is essentially colorless and may be used as a topical cosmetic or pharmaceutical preparation as well as an additive in food preparations. In addition, a method for producing substantive amounts of phytoene and phytofluene from carotenoid producing organisms is described as well.

15 Claims, 1 Drawing Sheet

CAROTENOID PREPARATION

This application is a continuation of Ser. No. 09/786,394 filed May 18, 2001, now U.S. Pat. No. 6,383,474 which is a 371 of PCT/IL99/00478 filed on Aug. 5, 1999.

FIELD OF THE INVENTION

The present invention relates to a carotenoid comprising preparation. The preparation of the invention can be used in food, in cosmetics, in a variety of medicinal uses, etc. The invention also concerns a method for the production of the carotenoids.

BACKGROUND OF THE INVENTION

Carotenoids are pigments produced by microorganisms, fungi and plants, and used by them as antioxidants and protectants against excessive radiation. The most widely used carotenoids in food, medical preparations or cosmetics are β-carotene and lycopene. β-Carotene and lycopene are sensitive to light and oxidation, a property which considerably limits their use and shortens shelf-life of products containing them (in: Carotenoids, Chemistry and Biology, Krinski, N. I., Matthews-Roth, M. M., Taylor, R. F., (Eds), Planum Press, New York, London, 1989). In addition, β-carotene and lycopene have a distinctive orange color and this color has a serious limitation for a variety of cosmetic or food applications.

Phytoene (7, 8, 11, 12, 7', 8', 11', 12'-octahydro-γ,γ-carotene) and phytofluene (15Z, 7, 8, 11, 12, 7', 8'-hexahydro-γ, γ-carotene), are carotenoids (C-40 isoprenoids chain) which are precursors in the biosynthetic pathway which leads to the production of β-carotene, lycopene and other carotenoids (phytoene is the first carotenoid-specific precursor and phytofluene is produced therefrom in a subsequent desaturation step). Phytoene is completely colorless whereas phytofluene has a slight yellowish color. Japanese Patent Application No. 90-40520, disclosed that the introduction of a DNA sequence yielding expression of phytoene into certain transfected cancer cells, resulted in inhibition of their growth and in inhibition in the activation of Epstein Barr virus (EBV).

SUMMARY OF THE INVENTION

In accordance with the present invention it was shown that phytoene and phytofluene possess anti-oxidative properties and furthermore are capable of absorbing ultra violet (UV) light. In addition, although having these properties, phytoene and phytofluene were found to be much more stable to oxidation than, for example, β-carotene. These findings led to the realization that phytoene and phytofluene in combination could be useful in the prevention of environmentally induced damage of various kinds.

Thus, in accordance with the invention there is provided a composition comprising, an amount of phytoene and an amount of phytofluene, effective in combination in the prevention of damage resulting from oxidation and from exposure to UV light.

In accordance with the invention, the term "damage" is to be understood as any damage resulting from a variety of oxidative agents such as oxygen itself, hydroxyl radical, hydrogen peroxide, other free radicals, ozone etc., or from any kind of harmful UV irradiation, such as UVA and UVB irradiation. The damage would depend upon the target for which the preparation is used. Thus, if the preparation is used on skin, damage may be any skin damage such as burns, blisters, damage appearing after chronic exposure to sun, e.g. premature aging of the skin, etc. When the preparation is used as a food preservative, such damage may be in the form of a decrease in product stability, chemical modification resulting for example in rancidity, accelerated aging, etc.

In accordance with a preferred embodiment of the invention there is provided a topical skin composition for protecting the skin against environmental hazards, comprising phytoene and phytofluene in an effective amount such that, in combination, these carotenoids exert an oxidation-protecting and UV-protecting effect on the skin.

The term "environmental hazards" relates to any environmental agent which can exert damage such as UV radiation or oxidative agents.

The term "effective amount" should be understood to mean an amount of phytoene and an amount of phytofluene which, when administered in combination, achieves the desired protective effect.

The phytoene and phytofluene in the composition of the invention may each be either in their trans or in their cis forms.

The weight ratio between the phytoene and phytofluene in the composition of the invention can range between about 200:1 to about 1:200, respectively, typically between about 50:1 to about 1:50, about 10:1 (phytoene:phytofluene) being a particular example. The above ratios of phytoene to phytofluene may be reached either by using an extract which contains both carotenoids in the desired ratio, by adding an additional amount of one of the carotenoids to an extract comprising both carotenoids so that the desired ratio is obtained or by mixing the two separate carotenoids (each obtained by any of the methods mentioned or described above and below) to reach the desired ratio between them.

One of the novel features of the inventive composition is that while possessing the above noted properties, the combination of phytoene and phytofluene is essentially devoid of any color (but for a slight yellowish hew, hardly visible, of the phytofluene). The fact that the composition is essentially colorless ensures that these carotenoids will not have any effect on the aesthetic properties of the preparation comprising them. In addition, the lack of absorbance of light in the visible range (which is a manifestation of the fact that they are essentially colorless) renders them stable to degradation under visible light.

The preparation may, in accordance with the above noted preferred embodiment, be used as a topical cosmetic or pharmaceutical preparation in order to protect the skin from environmental hazards such as those described above including UV (UVA and/or UVB) irradiation or damages which can be effected by a variety of oxidative agents. A topical composition of the invention may be in the form of a gel, an oil-in-water or water-in-oil emulsion, a salve or ointment, etc.

In accordance with another embodiment, the composition may be used as an additive in food preparations, e.g. serving as a preservative to protect against oxidation of the various food ingredients, e.g. of oils or fats.

At times, the composition of the invention may comprise additional components which do not substantively change the basic characteristics of the composition. One example of such a component is zetacarotene (7,8,7',8'-tetrahydro-γ, γ-carotene).

The composition of the invention may obviously, depending on its use, comprise also other ingredients, cosmetical or pharmaceutical acceptable carriers, preservatives, other antioxidants, various pharmaceutically or cosmetically active ingredients such as a topically acting drugs, etc.

In accordance with one preferred embodiment, the composition comprises also a hydrophobic carrier, which may be selected from oils typically used in the cosmetic, pharmaceutical or food industry, such as vegetable, mineral or synthetic oils.

The phytoene and phytofluene may be obtained from a variety of sources. Typically, they may be obtained from organisms that produce carotenoids, such as a variety of plants, various algae, and particularly micro algae *Dunaliella* sp, being a specific example. Very low amounts of phytoene and phytofluene have been produced by β-carotenoid producing organisms. To obtain even such low amounts of the carotenoids, the organisms were grown under dim light conditions. In accordance with the invention, a method is provided which enables to yield substantive amounts of at least one of phytoene or phytofluene from such carotenoid producing organisms. The term "substantive amounts" relates to an carotenoid producing organisms. The term "substantive amounts" relates to an amount of phytoene or an amount of phytofluene ranging from about 0.1 mg/l culture to about 30 mg/l culture typically between about 1 mg/l to about 20 mg/l. When the carotenoid producing organism is the algae *Dunaliella* sp., the typical amount of phytoene and phytofluene which may be produced is between about 1 mg/l to about 15 mg/l. In accordance with the method of the invention, the carotenoid producing organism, typically algae, may be grown under various kinds of conditions.

In accordance with one embodiment of this aspect of the invention, the carotenoid producing organisms are grown outside, for example, in the case of *Dunaliella* sp. in outside pools in a growth medium comprising sea water and recycled salt water at a temperature of between about 10° C. to about 40° C. The organisms may be grown under sunlight at an extent of between 80% shade to full sunlight. By a preferred embodiment, the carotenoid producing organisms are grown under bright light ranging from about 40% shade to full sunlight.

By an additional embodiment, the carotenoid producing organisms are grown in a growth culture, typically, in a fermentor and typically at room temperature in which case the growth medium will typically comprise various salts and minerals in different combinations (see, for example, Example 1.1 below). In accordance with this embodiment, the organisms are grown under broad spectrum light (light spanning over a substantive portion of visible light) of above about 10 W/m$^2$ and which may range from about 10 W/m$^2$ to about 200 W/m$^2$.

In accordance with the method of the invention, substantive amounts of phytoene and/or phytofluene are typically produced following several days of growth of the organism (e.g. about 4 to 6 days).

The phytoene and phytofluene are obtained under conditions which favor the accumulation of phytoene and phytofluene in cells of the organisms, typically by growing a β-carotene-producing organism in the presence of carotenoid-biosynthesis inhibitors, which are inhibitors that can act in subsequent reaction steps in the biochemical pathway of the production of carotenoids. One example of inafter: "the 4-chloro inhibitor"). When the source of phytoene and phytofluene is the micro algae *Dunaliella*, the 4-chloro inhibitor is typically included in the growth medium in a concentration of about 0.1 μM (Ben-Amotz et al., *Plant Physiol* 86:1286, 1988). Other inhibitors which may be used are, for example, J334, (Ben-Amotz et al. Supra) Sandoz H 6706 (Kümmel, H. W. et a., Z. Naturforsch 30c, 333, 1975), di-phenyl-amine (DPA) (Foppen F. H., *Ann. Ist. Super. Sanita*, 439, 1969) and nicotine (Shaish et al, *Plant Cell Physiolo* 31:689, (1990)).

In accordance with one embodiment of this aspect of the invention there is thus provided a method for preparing a composition comprising at least one of phytoene or phytofluene, comprising the steps of
(i) incubating a carotenoid producing organism in a growth culture under broad spectrum light having an intensity of above about 10 W/m$^2$ in the presence of one or more carotenoid synthesis inhibitors;
(ii) growing said carotenoid producing organisms until the level of at least one of phytoene or phytofluene is between about 1 mg/l culture to about 50 mg/l culture; and
(iii) separating said organisms from the culture.

In accordance with an additional embodiment of this aspect of the invention there is provided a method for preparing a composition comprising at least one of phytoene or phytofluene, comprising the steps of:
(i) Incubating a carotenoid producing organism in a growth culture under sunlight at an extent between about 80% shading to full sunlight in the presence of one or more carotenoid synthesis inhibitor;
(ii) Growing said carotenoid producing organisms until the level of at least one of phytoene or phytofluene is between about 1 mg/l culture to about 50 mg/l culture; and
(iii) separating said organisms from the culture.

In accordance with this aspect of the invention, the phytoene and phytofluene obtained in the grown organisms may be used without being separated In accordance with this aspect of the invention, the phytoene and phytofluene obtained in the grown organisms may be used without being separated from the dry matter of the producing organism. However, in accordance with a preferred embodiment, following separation of the carotenoid producing organism from the culture, a preparation is further prepared from the organisms comprising phytoene, phytofluene or both. Typically, the preparation is an extract which may be prepared from the carotenoid producing organisms by any of the extraction methods known in the art such as, for example, by ethanol:hexane extraction.

In accordance with the method of the invention, typically, both phytoene and phytofluene are obtained from the carotenoid producing organism and the ratio of phytoene to phytofluene may vary according to the conditions under which the organism was grown and, when a preparation is prepared, the type of methods used for obtaining the preparation. At times, however, under certain conditions, growing the carotenoid producing organism in accordance with the method of the invention is may result in obtaining mostly one or only one of the two carotenoids.

In accordance with the invention it was also found that the carotenoids ratio may further be enhanced in favor of phytoene and phytofluene by the addition of active charcoal during carotenoid extraction. Charcoal may be added when an inhibitor is used as well as when the carotenoid producing organism is grown without the inhibitor. The charcoal is later filtered out from the culture or preparation using any of the known centrifugation or filtration methods.

In addition to the above, in accordance with the invention the carotenoids in the composition of the invention may also be synthesized by any of the known chemical or biochemical methods or recombinant methods. Chemically, phytoene can be synthesized, for example, from two geranylgeranyl pyrophosphates (C-20), in a reaction which may be mediated by phytoene synthase. The geranylgerranyl pyrophosphate can be obtained directly, by the conversion of mevalonic acid or by the condensation of pyrovate and glyceraldehyde-3-phosphate. Phytofluene can be synthesized by desaturation of phytoene, a reaction which may be mediated by phytoene desaturase. Recombinant methods include, for example, the mutagenesis of enzymes which are active downstream to phytofluene. Such synthesized phytoenes and phytofluenes will have activities which are substantively similar to the activities of the phytoene and phytofluene obtained from organisms that produce carotenoids as explained above.

The stability of the carotenoids in the composition of the invention can be tested by irradiating the carotenoid composition by light and/or exposing the composition to oxygenating agents. The effect of such treatments on the carotenoids in the compositions of the invention, is less than the effect of such treatments on other carotenoids such as, for example, β-carotene. In prior art compositions containing an effective amount of carotenoids, such treatment typically result in degradation of the carotenoids, manifested for example by change in light absorbance, i.e. color. The anti-oxidative effect of the composition of the invention can be determined, for example, by determining the anti-oxidation protection effect on DNA (Salles et al., *Anal. Biochem.*, 232:37, 1995).

The invention will now be illustrated further in the following description of the non-limiting specific embodiments.

EXAMPLES

I. Materials and Methods

1. Growth Mediums

Figure 1:
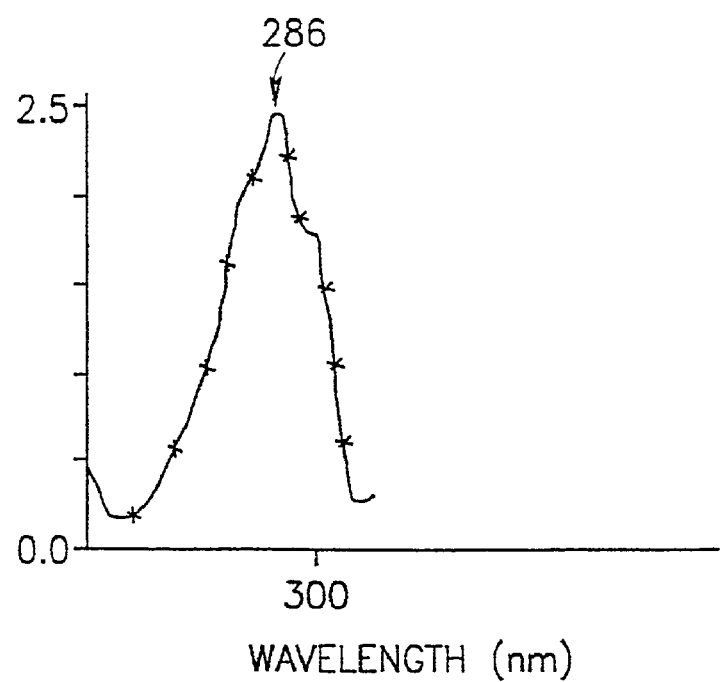
FIG. 1 shows the UV absorbance spectra of a composition comprising phytoene extracted from *Dunaliella* sp. grown with the 4-chloro inhibitor.

The following growth mediums were used:

1.1 A growth medium comprising:

$MgSO_4$, 5 mM; $CaCl_2$, 0.2 mM; $KH_2PO_4$, 0.2 mM; $FeCl_3$+$Na_2EDTA$, 2 μM+5 μM; $MnCl_2$, 7 μM; $CuCl_2$, 1 μM; $ZnCl_2$, 1 μM; $CoCl_2$, 1 μM; $(NH_4)_6MO_7O_{24}$, 1 μM; NaCl, 1M; $NaHCO_3$, 50 mM; KCl, 5 mM.

The growth medium is typically used for growth of carotenoid producing organisms inside under artificial conditions.

1.2 A growth medium comprising sea water and recycled salt water in an amount which results in 2M salinity. Such a medium is typically used while growing a carotenoid producing organism outside under sunlight. The final pH of the growth mediums was 7.0 to 8.0.

2. Chemicals

β-Carotene biosynthesis inhibitor 4chloro-5(methylamino)-2-(3-(trifluoromethyl)phenyl)-3(2H)-pyridazinone. The 4-chloro inhibitor was used for phytoene and phytofluene production. The range of concentration of the 4-chloro inhibitor was between about 0.07 μM to about 0.5 μM.

Untreated active charcoal was used to increase the ratio of phytoene and phytofluene to other carotenoids. The charcoal was filtered out from the extract at the final steps of preparation of the extract.

Various commercially used oils were used to dissolve the phytoene and phytofluene.

3. Growth of *Dunaliella* sp.

The algae *Dunaliella* sp was grown under one of the following conditions:

3.1 In the growth medium described in 1.1 above in a fermentor at room temperature under artificial lighting which altered in the range of between dim light (from about 1 $W/m^2$) to bright light (above about 10 $W/m^2$), typically under light of above 10 $W/m^2$ in the range of between 10 W/m to about 200 $W/m^2$.

3.2 In outside pools at a temperature of between about 10° C. to about 40° C. under light conditions in the range of between 80% shade to full sunlight, typically between 40% shade to full sunlight.

4. Carotenoids Extraction Method

Phytoene and phytofluene were produced by inhibition of β-carotene synthesis in the algae *Dunaliella* sp. By the 4-chloro inhibitor at a concentration of 0.07 μM to 1.0 μM.

The algae were collected after four to six days of growth of the algae either outdoors or indoors as described above and the cell pellet was extracted with Or ethanol:hexane (1:2) v/v. Ethanol was first added to the cell pellet at algae:ethanol ratio of at least 1:10. At this stage basic hydrolysis of ester bonds is performed by the addition of 0.5M NaOH with stirring for at least 30 min. Ethanol:hexane phase separation is achieved by the addition of NaCl at adequate quantity. The hexane fraction was analyzed spectrophotometrically.

Hexane was dried under vacuum and the carotenoids were re-dissolved in hexane or oil.

5. Spectrophotometric Analysis

Absorption spectra of the phytoene and phytofluene extract was determined using Hewlett Packard 8452A Diode Array Spectrophotometer.

6. Stability of Phytoene and Phytofluene Under Aerobic Conditions in UV Lights and Various Incubation Temperatures Stability of the carotenoids in the various temperatures was determined by long-term incubation of phytoene and phytofluene in several types of oils and solvents at 4° C., 23° C., 30° C. and 60° C. The amount of phytoene and phytofluene left was determined spectrophotometrically. The percent of phytoene and phytofluene left was calculated as follows:

$$\frac{\text{Phytoene and phytofluene after treatment(mg/ml)}}{\text{Phytoene and phytofluene before treatment(mg/ml)}} * 100 =$$

% PH and PF left

Stability under UV lights (254 nm, 365 nm, 254+365 nm), for 30 mins. at 300/310 μw/$cm^2$ was determined.

7. Stability of Phytoene and Phytofluene Under Aerobic Conditions in Visible Light Stability of phytoene and phytofluene under visible light was measured under sunlight (full sun summer day in Rehovot, Israel, at noon) filtered through "hot mirror" (Andover Corporation, Salem, N.H., transmittance 400-650 nm) filter. Samples were dissolved in ethanol, exposed to light for 30-150 min and then extracted in hexane after basic hydrolysis (as in extraction method above). Phytoene, phytofluene and beta-carotene amounts were measured spectrophotometrically, and percentage lefts were calculated as in section 5 above.

8. Anti-free Radical Activity 8.a Quenching of Hydroxyl Radicals:

The ability of the compound to quench the activity of hydroxyl radicals (°OH) was measured by Electron Paramagnetic Resonance (EPR), by comparing the signal intensity with and without the compound. Hydroxyl radicals were generated by decomposition of hydrogen peroxide by iron [(FeSO$_4$) Fenton reaction]. The °OH is trapped by the DMPO to provide a DMPO-OH adduct, which presents a characteristic signal in EPR. The compound, composed of phytoene and phytofluene at a ratio of 6.66:1 respectively, was added to the system in tree final dilutions of 1/20, 1/50 and 1/200.

Since various substances can reduce the signal, not by trapping of the °OH but by addition to the DMPO-OH adduct, it is necessary to also evaluate the signal when the product is added after the Fenton reaction (post-addition). The trapping capacity of the hydroxyl radical is evaluated theoretically by the difference between the value of the EPR signal corresponding to pre-addition of the product and the value of the signal resulting from post-addition.

8.b DNA Protection by Anti-oxidation Effects:

DNA protection by the anti-oxidation effect of the compound was examined based on the method of Salles et al. (Supra). In the test the protective effect of the compound against Reactive Oxygen Species (ROS) generated oxidative DNA damage was measured, by quantifying the inhibition of DNA lesions formation using plasmid DNA target.

II. Results

Example 1

Phytoene and Phytofluene Production

Phytoene and phytofluene were produced from the algae *Dunaliella* sp. by growing the algae in the presence of 0.1-0.5 μg of the β-carotene biosynthesis 4-chloro inhibitor as described above. The cultures were then extracted and the extract was dried by evaporation and re-dissolved in hexane or oil. No residues of the 4-chloro inhibitor were detected in the extracted carotenoids.

Figure 2:
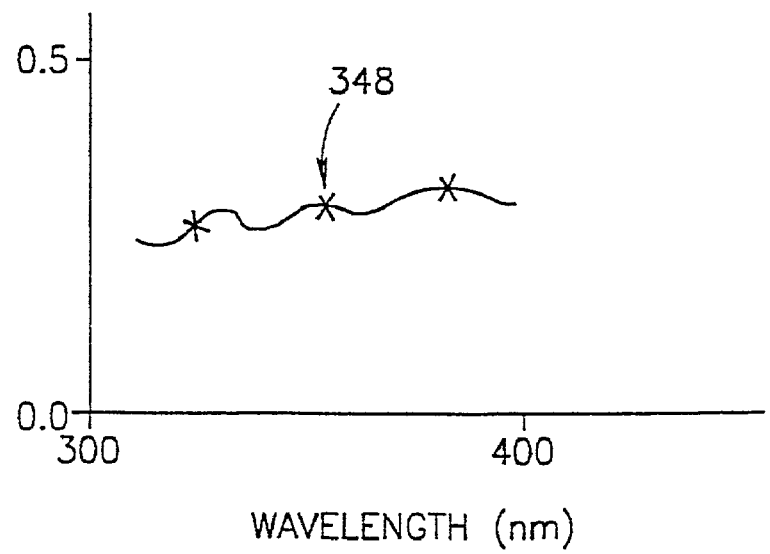
FIG. 2 shows the UV absorbance spectra of phytofluene extracted from *Dunaliella* sp. grown with the 4-chloro inhibitor.

As seen in FIG. 1, the main absorbance peak of phytoene was found to be at 286 nm (UVB) and as seen in FIG. 2, the main absorbance peak of phytofluene was found to be at 348 nm (UVA). As expected, the main absorbance peak for β-carotene was at 450 nm. β-Carotene was reduced due to the synthesis inhibition while phytoene and phytofluene increased.

Example 2

Example for the Stability of the Extracted Phytoene and Phytofluene in UV Lights The stability of the phytoene and phytofluene extracts obtained as explained in Example 1 above was determined by spectrophotometric analysis. Phytoene and phytofluene were dissolved in hexane or oil. The absorbance of the preparation is determined in 220-600 nm and the amount of each of the above carotenoids in each sample is calculated to determine the percent of the carotenoids measured after irradiation of the extract divided by the amount of the same carotenoid which was measured in the extract before exposing it to irradiation (see Materials and Methods 5 above). The stability of the phytoene and phytofluene was measured by the exposure of the extract both to UVA light (365 nm) and UVB light (254 nm) irradiation as well as to a combination of UVA and UVB irradiation.

As seen in Table 1 below, phytoene and phytofluene dissolved in oil or hexane were very stable after exposure to UVA, UVB or UVA+B irradiation.

TABLE 1

PH and PF stability in UV irradiation (30 minutes exposure)

| | Darkness PH and PF (% left)[1] | 254 nm PH and PF (% left) | 365 nm PH and PF (% left) | 254 nm + 365 nm PH and PF (% left) |
|---|---|---|---|---|
| PH left[1] in hexane | 100 | 92.2 | 98.7 | 92.4 |
| PF left[1] in hexane | 100 | 92.6 | 101.5 | 99.0 |
| PH left[1] in oil | 100 | 100 | 100 | 101 |
| PF left[1] in oil | 100 | 90 | 88 | 98 |

[1]Percent of PH or PF left is the amount of material (mg/ml) measured after irradiation divided by the amount of material measured before treatment multiply by 100.

The stability of phytoene and phytofluene under different temperature conditions (4° C., 23° C., 30° C. and 60° C.) in hexane or in other various commercially used oils was also measured.

The measurements were carried out over a period of four months.

Phytoene and phytofluene were found to be stable in the entire measured temperature range with no substantial effect of the kind of oil in which the carotenoids were dissolved.

Example 3

Stability of the Extracted Phytoene and Phytofluene in Visible Light

Stability of phytoene and phytofluene was compared to that of beta-carotene stability (as explained in materials and methods) under visible light. The absorbance of the preparation is determined in 220-600 nm wavelength and the amount of each of the above carotenoids in each sample is calculated to determine the percent of the carotenoids measured after irradation of the extract compared to measurements prior to irradiant (see example 2 above).

As shown in table 2, exposure to visible high intensity light cause significant higher degradation of beta-carotene compared to phytoene and phytofluene.

TABLE 2

PH and PF stability in visible light (15-150 min exposure)

| Time of exposure (min) | Phytoene (% left) | Phytofluene (% left) | Beta-carotene (% left) |
|---|---|---|---|
| 0 | 100 | 100 | 100 |
| 30 | 54.46 | 66.13 | 25.00 |
| 90 | 20.33 | 50.42 | 11.36 |
| 120 | 15.70 | 41.33 | 9.47 |
| 150 | 13.64 | 33.06 | 5.68 |

Example 4

Anti Free Radical Activity 4.a Quenching of Hydroxyl Radicals:

Quenching of hydroxyl radicals was measured by EPR as explained in materials and methods. The results obtained (Table 3) indicate a dose-dependent trapping activity of the hydroxyl radical by the product.

TABLE 3

| Product final concentration (mg/ml) | Intensity of EPR signal (arbitrary units) | Intensity of the EPR signal after post-addition (arbitrary units) | % of hydroxyl radicals trapping |
|---|---|---|---|
| 0 | $2.82 \times 10^6 \pm 0.07$ | | |
| 0.001 | $0.34 \times 10^6 \pm 0.04$ | $2.19 \times 10^6 \pm 0.13$ | 66 |
| 0.0004 | $0.58 \times 10^6 \pm 0.02$ | $1.94 \times 10^6 - \pm 0.05$ | 48 |
| 0.0001 | $1.26 \times 10^6 \pm 0.10$ | $2.19 \times 10^6 \pm 0.13$ | 24 |

The product was composed of phytoene and phytofluene at a ratio of 6.66:1 respectively at an initial concentration of phytoene 0.02 mg/ml and phytofluene 0.003 mg/ml.

The average value of each result corresponds to three measurements.

4.b Anti Oxidation Effect:

DNA protection by the anti oxidation effect of the phytoene and phytofluene extracts was determined based on the Salles method (Supra) as explained in Materials and Methods 7.b above.

As seen in Table 4 below, phytoene and phytofluene obtained as described above were capable of protecting against hydroxyl radicals.

TABLE 4

PH and PF anti oxidation activity

| Compound | Concentration µg/ml | % of inhibition in the presence of ROS | % of non specific inhibition | % of specific inhibition | Concentration giving 50% of activity |
|---|---|---|---|---|---|
| Phytoene and phytofluene | 140 | 86 | 24 | 62 | 11.2 µg/ml |
| | 14 | 74 | 19 | 55 | |
| | 1.4 | 6 | 7 | 1 | |
| | 0.14 | 1 | 1 | 0 | |
| Positive control | 1000 | 88 | 9 | 79 | 80 µg/ml |
| | 100 | 69 | 11 | 58 | |
| | 10 | 5 | 0 | 5 | |
| | 1 | 4 | 0 | 4 | |

Example 5

Protective Effects on DNA by Phytoene and Phytofluene

Genotoxic Effect

The genotoxicity is measured as the induction of DNA repair synthesis activity and is expressed by the ratio (R): while $R \leqq 2$ indicate no toxic effect $$R = \frac{\text{Relative Light Unit of the sample}}{\text{Relative Light Unit of the solvent alone}}$$

As seen in Table 5 below, phytoene and phytofluene are not genotoxic.

The R parameter is significantly less than 2 (protective effect) and much smaller in comparison with the positive control, which is a known genotoxic compound.

TABLE 5

Genotoxic effect of phytoene and phytofluene

| Compound | Concentration (µg/ml) | Genotoxicity (Ratio)* |
|---|---|---|
| Phytoene and phytofluene | 140 | 0.92 |
| | 14 | 1.11 |
| | 1.4 | 1.18 |
| | 0.14 | 0.05 |
| MMS-(positive control) | 10 mM | 6.26 |
| | 2 mM | 2.44 |

*See above

Example 6

The following are examples of compositions that may be used in accordance with the invention:

| | | |
|---|---|---|
| A | Emulsified gel of O/W (topical route): | |
| | Carbopol 981 (marketed by Goodrich) | 0.6 g |
| | Ethyl alcohol | 15 g |
| | Volatile silicone oil | 3 g |
| | Purcellin oil | 7 g |
| | Preserving agent | 0.3 g |
| | Perfume | 0.4 g |
| | Triethanolamine | 0.2 g |
| | Phytoene | 0.01 g |
| | Phytofluene | 0.001 g |
| | Demineralized water.qs | 100 g |
| B | Anhydrous gel (topical route): | |
| | Propylene glycol | 25 g |
| | Hydroxyethyl cellulose | 0.8 g |
| | Polyethylene glycol | 12 g |
| | Phytoene | 1 g |
| | Phytofluene | 1 g |
| | Absolute ethanol.qs | 100 g |
| C | Emulsion of O/W type (topical route): | |
| | Liquid paraffin | 6 g |
| | Liquid lanolin | 3 g |
| | Arlacel 165 (marketed by Atlas) | 6 g |
| | Tween 60 (marketed by Atlas) | 2 g |
| | Cetyl alcohol | 1.2 g |
| | Stearic acid | 2.5 g |
| | Volatile silicone oil | 10 g |
| | Triethanolamine | 0.1 g |
| | Preserving agent | 0.3 g |
| | Antioxidants | 0.3 g |
| | Phytoene | 0.3 g |
| | Phytofluene | 0.2 g |
| | Demineralized water.qs | 100 g |
| D | Cream containing liposomes (topical route): | |
| | Sunflower oil | 35 g |
| | Cetyl alcohol | 4 g |
| | B-sitosterol | 4 g |
| | Dicetyl phosphate | 0.5 g |
| | Preserving agent | 0.3 g |
| | Parfume | 0.6 g |
| | Carbopol 981 (marketed by Goodrich) | 0.2 g |
| | Triethanolamine | 0.2 g |
| | Sphingosine | 005 g |
| | Phytoene | 0.00001 g |
| | Phytofluene | 0.000001 g |
| | Demineralized water. qs | 100 g |
| E | Per os composition: | |
| | Talc | 5 g |
| | Aerosil 200 | 5 g |
| | Stearate de Zn | 5 g |
| | Phytoene | 0.0000015 g |
| | Phytofluene | 0.000001 g |
| | Lactose qs | 400 g |
| F | Emulsion W.O (topical route): | |
| | Protegin (marketed by Goldschmidt) | 19 g |
| | Glycerine | 3 g |

-continued

| | |
|---|---|
| Vaseline oil | 8 g |
| Phytofluene | 0.5 g |
| Phytoene | 0.5 g |
| Sulfate de Mg | 0.5 g |
| Perfume | 0.8 g |
| Preserving agent | 0.2 g |
| Water.qs | 100 g |

The invention claimed is:

1. A protective composition consisting essentially of a mixture of phytoene and phytofluene, wherein the mixture is in an amount sufficient to prevent damage resulting from oxidation or from exposure to UV light, and wherein the weight ratio between the phytoene and phytofluene in the protective composition is in the range of 200:1 to 1:200, respectively and said composition is essentially colorless and has an absorbancy spectrum at the UV wave range.

2. An additive composition for food consisting essentially of an amount of phytoene and an amount of phytofluene, effective in combination in the prevention of damage resulting from oxidation or from exposure to UV light, wherein the weight ratio between the phytoene and phytofluene in the additive composition is in the range of 200:1 to 1:200, respectively and said additive composition is essentially colorless and has an absorbancy spectrum at the UV wave range.

3. An additive composition for food preparation consisting essentially of: a compound selected from the group consisting of phytoene, phytofluene, and a combination thereof, wherein the weight ratio between the phytoene and phytofluene in the additive composition is in the range of 200:1 to 1:200, respectively and the compound is in an amount sufficient to prevent damage resulting from oxidation or exposure to UV light, and wherein said additive composition is essentially colorless and has an absorbancy spectrum at the UV wave range.

4. The additive according to claim 2, wherein the weight ratio between the phytoene and phytofluene in the composition is in the range of 50:1 to 1:50, respectively.

5. The additive according to claim 2, wherein the weight ratio between the phytoene and phytofluene in the composition is in the range of 10:1 to 1:10, respectively.

6. The additive according to claim 2, containing a hydrophobic carrier.

7. An additive composition for food consisting essentially of a mixture of phytoene, phytofluene and zetacarotene, wherein the mixture is in an amount sufficient to prevent damage resulting from oxidation or from exposure to UV light, and wherein the composition is essentially colorless and has an absorbancy spectrum at the UV wave range.

8. A composition according to claim 1, wherein said phytoene or phytofluene are prepared by chemical synthesis.

9. A composition according to claim 1, wherein said phytoene or phytofluene are prepared by recombinant methods.

10. A method for preventing damage to food resulting from oxidation or exposure to UV light, comprising: adding a food additive composition to the food, wherein the additive composition consists essentially of phytoene and phytofluene in an amount sufficient to treat or prevent damage resulting from oxidation or exposure to UV light, and wherein said composition is essentially colorless and has an absorbancy spectrum in the UV range.

11. A process for preparing a food additive, comprising obtaining a preparation consisting essentially of a substantive amount of phytoene, phytofluene, or a combination thereof, wherein the preparation is obtained from a carotenoid-producing organism, and wherein the preparation is enriched during growth of the carotenoid producing organism or during extraction of the phytoene, phytofluene, or combination thereof.

12. A food preservative composition, consisting essentially of phytoene, phytofluene, or mixtures thereof, effective in the prevention of damage resulting from oxidation or from exposure from UV light, and wherein the composition is essentially colorless and has an absorbancy spectrum at the UV wave range.

13. The composition of claim 1, wherein the phytoene and the phytofluene are obtained from a carotenoid producing organism.

14. The composition of claim 13, wherein the carotenoid producing organism is a micro algae.

15. The composition of claim 14, wherein the micro algae is a *Dunaliella* sp.

* * * * *